United States Patent [19]
Stafford et al.

[11] 3,937,953
[45] Feb. 10, 1976

[54] NON-CONTACTIVE PROXIMITY SENSOR SYSTEM UTILIZING NUCLEONIC RADIATION FLUORESCENCE
[75] Inventors: R. Wayne Stafford; William H. Tobey; Benton C. Clark, III, all of Littleton, Colo.
[73] Assignee: Martin Marietta Corporation, New York, N.Y.
[22] Filed: Nov. 12, 1973
[21] Appl. No.: 415,188

[52] U.S. Cl. .................. 250/272; 250/336; 250/394
[51] Int. Cl. ........................................... G01n 23/20
[58] Field of Search ........... 250/272, 273, 336, 394, 250/460

[56] References Cited
UNITED STATES PATENTS
3,285,533  11/1966  Jernigan, Jr. .................. 250/336 X
3,316,392  4/1967   Bailey et al. ................... 250/272 X
3,562,525  2/1971   Constantine et al. ............... 250/272

Primary Examiner—Archie R. Borchelt
Attorney, Agent, or Firm—Sughrue, Rothwell, Mion, Zinn & Macpeak

[57] ABSTRACT

A proximity sensor utilizing nucleonic radiation fluorescence to detect the presence, position and/or distance of a target object from a monitoring object. The inventive system has particular application in collision avoidance systems for subsatellites, final docking alignment systems in spacecraft applications, collision avoidance systems for teleoperated manipulative arms, homing devices for manipulative devices as well as hazard detection systems for planatary rovers. Where necessary, the target object is fitted with cooperative radiation fluorescent material. The monitoring object looks for and detects the preselected fluorescence, thus discriminating between radiation emitted by the target object and extraneous radiation.

4 Claims, 4 Drawing Figures

NON-CONTACTIVE PROXIMITY SENSOR SYSTEM UTILIZING NUCLEONIC RADIATION FLUORESCENCE

BACKGROUND OF THE INVENTION

1. Field of the Invention

The invention is in the field of nucleonic radiation responsive measuring and detecting systems.

2. Prior Art

As is known, there are various types of instruments which are used to detect the presence, position and/or distance of a target body from a monitoring body. As used herein, the monitoring body is defined as that body which carries the detecting instrumentation. Typical examples of conventional type instruments are those which are barometric pressure, radar and radio waves to detect the target body. As explained in U.S. Pat. No. 3,508,046, issued Apr. 21, 1970 to Anton et al., instruments which make use of the above-listed phenomenons suffer serious disadvantages when the instruments are used to measure the distance between the target and monitoring bodies under certain conditions, especially where small distances are being measured.

As further explained in the Anton et al. patent, several of the problems with the above-listed types of range measuring instruments have been alleviated with the advent of a new type of range measuring apparatus which makes use of nucleonic radiation. In such range measuring devices, the monitoring body is fitted with a source of nucleonic radiation. Typical sources include those which produce alpha, beta, gamma or X-radiation. Conventionally, the source radiation is collimated, using a suitable radiation lens system, to thereby direct the radiation to a defined area on the target body. A portion of the transmitted radiation is reflected or back scattered from the target body surface and returned to the monitoring body where suitable detectors to produce an electrical signal proportional to the reflected radiation over a given time interval.

In accordance with the Anton et al teaching, the distance between the target and monitoring objects can be determined using a two detector system. The specifics of the distance measuring technique are set out in detail therein and need not be described herein.

A similar type distance measuring device, dependent upon reflected radiation from the target body, is described in U.S. Pat. No. 3,483,371 issued Dec. 9, 1969 to Canup et al. As with the Anton et al patent, radiation reflected from the target body and originating at the monitoring body, is detected and used for range measuring purposes.

Radiation responsive instruments have also been used to determine the orientation of a moving body in the atmosphere. Such an instrument is described in U.S. Pat. No. 3,557,366 issued Jan. 19, 1971 to Jernigan, Jr. Again, the detector is specifically responsive to radiation produced by the monitoring body and reflected from the target.

It is also known to use nucleonic radiation deflected from the surface of a terrestrial body for the purposes of terrestrial prospecting and terrain mapping. Examples of such techniques are described in U.S. Pat. No. 3,341,706 issued Sept. 12, 1967 to Swift et al. and U.S. Pat. No. Re. 26,335 issued Jan. 9, 1968 to Chope.

A problem with such radiation responsive instruments, whether they be used for object locating purposes or terrain analysis, is that they are susceptible to interference from extraneous radiation and particularly from reflected radiation emanating from non-target objects. To overcome this problem, vaarious additional sophisticated and expensive equipment has been utilized to counteract the unwanted reflections. For example, as indicated in the Anton et al patent, an extra detector and associated circuitry may be used in an attempt to alleviate the problem associated with extraneous reflections. The present invention solves the problem of unwanted reflections and extraneous radiation received by the detector without the need of additional sophisticated and expensive equipment.

SUMMARY OF THE INVENTION

The present invention is directed to an improved radiation responsive type monitoring system as well as to new applications for such systems.

Primarily, the present invention makes use of nucleonic radiation fluorescence rather than reflected radiation, in non-contactive proximity detection systems to determine the presence, position and/or distance of a target object from a monitoring object as well as for terrain analysis. An important advantage of the present inventive radiation fluorescence system over prior art radiation reflection systems is the subject system's inherent ability to discriminate between radiation from the target object and extraneous radiation, which may, for example, result from radiation reflected from non-target objects.

The apparatus, described more fully hereinbelow, has particular application to collision avoidance systems, to systems which control the final docking alignment of spacecrafts, homing devices for manipulative devices as well as homing and hazard detection systems for planatary rovers.

DETAILED DESCRIPTION OF THE PREFERRED EMBODIMENT

It is known that when some materials are excited with nucleonic radiation, such as X-rays, the radiation is absorbed causing the material to emit characteristic radiation during the time of radiation absorption. This phenomenon is generally known as fluorescence. The present invention makes use of this phenomenon to develop new and improved radiation responsive position and/or distance detecting systems as well as terrain analysis systems.

The primary teachings of the present invention will now be explained with reference to FIG. 1. It should be noted at this point, that while the present invention will herein be described with reference to systems which make use of X-ray sources, the inventionn is not so limited. It includes any system which directs radiation to a target body, said radiation causing corresponding characteristic fluorescence which is thereafter detected to develop information pertinent not only to the relative position of a target body with respect to a monitoring body, but also to the characteristics of the target body terrain composition.

Figure 1:
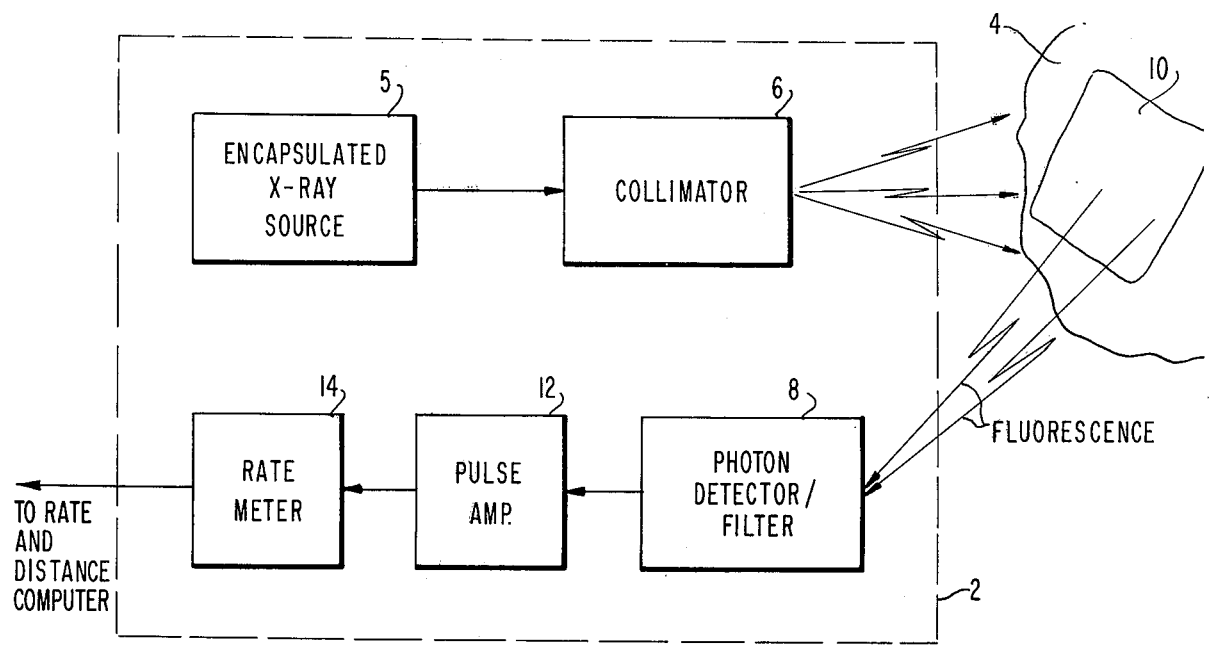
FIG. 1 is a block diagram of the preferred embodiment of the present invention.

Referring now to FIG. 1, numeral 2 denotes the monitoring object, which can be, for example, a spacecraft approaching a landing site 4, termed generally herein the "target object." The target object may be fitted, where necessary, with a cooperating X-ray fluorescence material 10, which fluoresces with characteristic radiation in response to being excited by radiation produced from a source on the monitoring object 2. In certain instances, the target itself may be comprised of material which fluoresces. For example, it is known that aluminum will fluoresce in response to X-rays. Thus, if the monitoring body is a spacecraft and the target body an aluminum space station, no special cooperative X-ray fluorescent material need by affixed to the target body.

Looking now more particularly to the monitoring object 2, it contains a conventional source of radiation 4, which in the preferred embodiment, is a source of X-rays. A collimator 6 operates in a conventional manner to focus the X-rays into a sharp narrow beam directed to a desired location 10 on the target body 4. When the X-rays impinge the cooperating fluorescent material 10, it is absorbed to stimulate fluorescence which is detected by a photon detector 8.

The detector 8 advantageously includes suitable radiation filters to block all but the expected fluorescence.

The output of the photon detector 8, passes through a pulse amplifier 12 and thence to a rate meter 14. The rate meter 14 may correspond to the rate meter described in the aforementioned Canup et al. patent and operated to producd a D.C. voltage which varies as a function of the rate of occurrence or intensity of the input pulses thereto. The output of the rate meter 14 is applied to a conventional rate and/or distance computer such as described in the Anton et al. and Canup et al. patents. The photon detector 8 and rate meter 14, are conventional and do not, per se, form a portion of the present invention.

Figure 2:
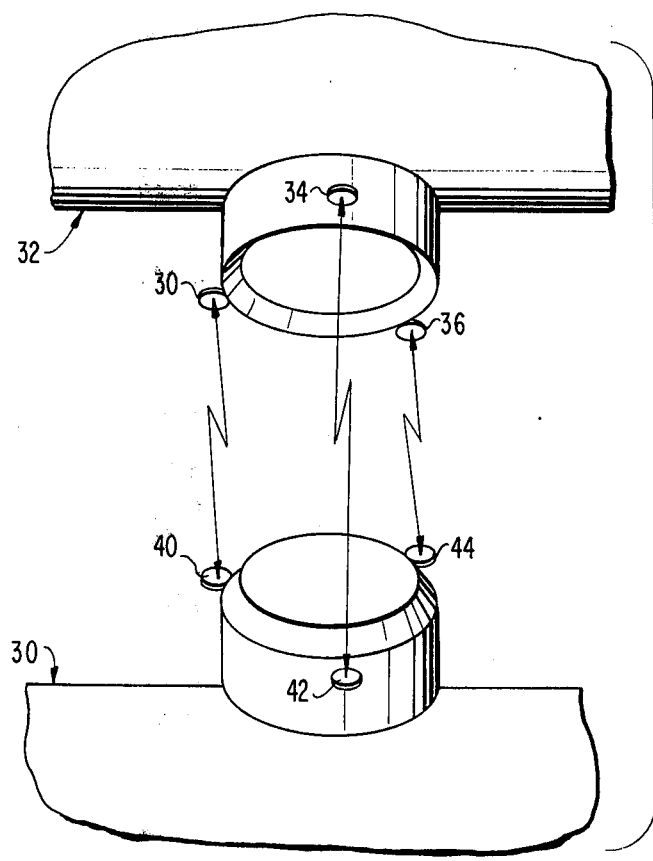
FIG. 2 illustrates a first application of the invention.

One application of the invention radiation fluorescence sensor is illustrated in FIG. 2. FIG. 2 schematically illustrates two large orbiting systems in the midst of a docking maneuver. The fluorescence sensor of the present invention can be used to provide accurate range and angle data during the critical one to two meters immediately prior to the docking of the two orbiting systems.

The spacecrafts would include, for example, three detector-target pairs and would make use of the detection $1/r^4$ sensitivity, where $r$ equals the distance between the orbiting bodies, to measure the range and angle between each detector-target pair.

More specifically, spacecraft 30, may include detector units 40, 42 and 44 each of which includes the apparatus indicated at 2 of FIG. 1. Spacecraft 32 on the other hand, would include cooperating targets 34, 36, and 38 each provided with a cooperating fluorescent material. To distinguish between the target pairs, the material coating each of the targets 34, 35 and 38 may be different thereby generating different characteristic fluorescence, after being converted into proportional electrical signals, could then easily be used with either manual or automatic closure-docking systems. The system's range and angle calculation capability, the fact that it is lightweight, utilizes low power (generally approximately 1 watt per sensor) is easy to calibrate, and has an inherent high capability to discriminate between docking targets and background objects and/or surfaces, make it virtually ideal for this application. At this point, it should be noted, that calibration is easily effectuated using dummy targets at known distances and angles in front of the sensor prior to each use.

Figure 3:
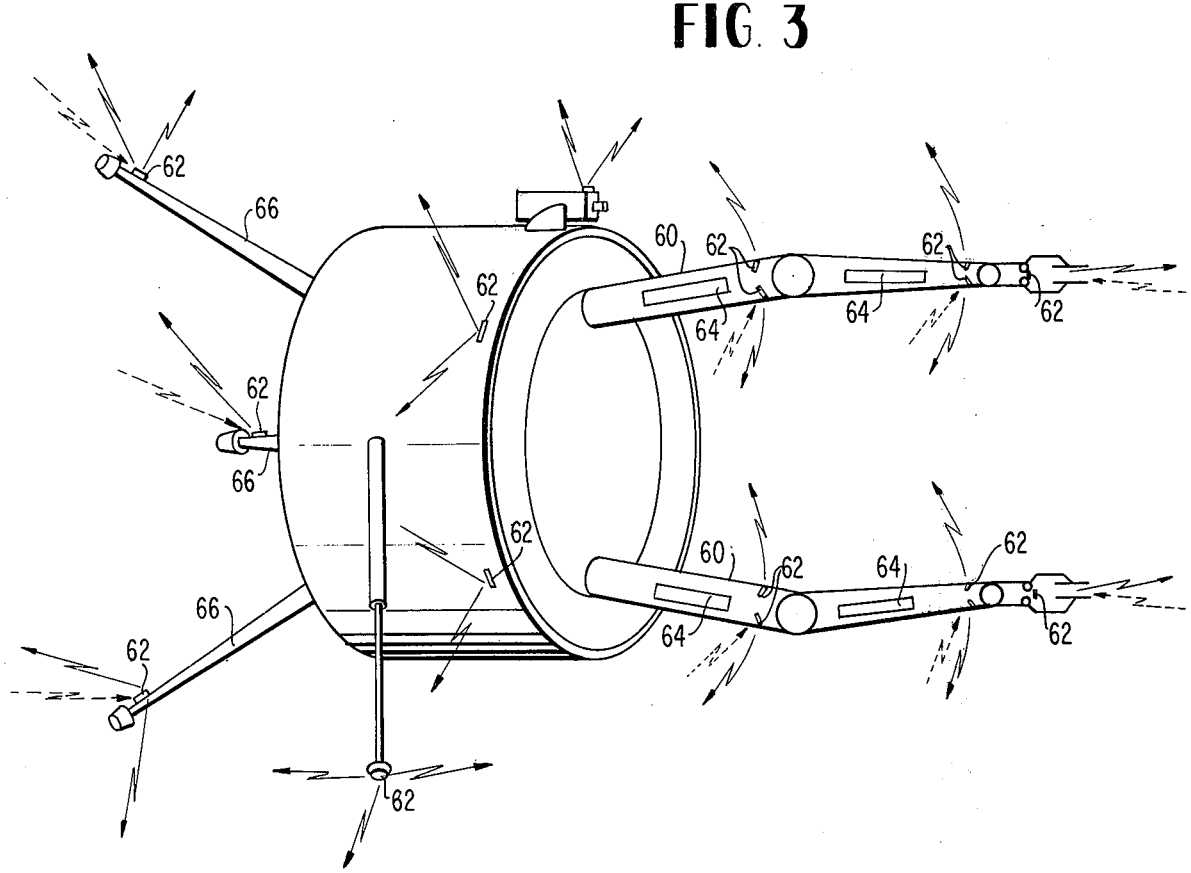
FIG. 3 illustrates a second application of the invention.

FIG. 3 illustrates another application of the inventive sensor system. This Figure illustrates a free flying spacecraft with teleoperated manipulative arms 60, fitted with radiation fluorescent detectors 62 and cooperating fluorescent material 64. The detectors 62 correspond to the detectors 2 of FIG. 1. The detector system may be used in this application as a safety device for collision avoidance, a standoff guidance sensor, a docking alignment reference, a station keeping sensor, as well as an integrated contamination-guidance sensor.

For example, standoff guidance of the free flying spacecraft can be achieved by propelling the spacecraft to equalize signal levels received by the sensors 62 on the three docking arms 66.

Unique docking ports or station keeping sites can be easily identified by utilizing identifying X-ray fluorescent materials around the docking sites and incorporating suitable filters with the photon detector 8.

Looking more specifically to the integrated contamination/guidance sensor feature of the invention, the fluorescent property allows the detector unit to analyze materials, possibly contaminants, in the field of view of the source radiation. This can be done simultaneously with standoff or station keeping when multi-spectral filters are incorporated with the detector apparatus.

With reference now to the teleoperated manipulative arms 60, they are provided with radiation fluorescent detectors 62 as well as cooperating X-ray material 64, to develop a safety device which prevents collision between arms as well as between the arm and work site objects. Potential collisions between multiple arms on a spacecraft or between an arm and a near object on the work site can be sensed by configuring the sensors as illustrated in FIG. 3.

Figure 4:
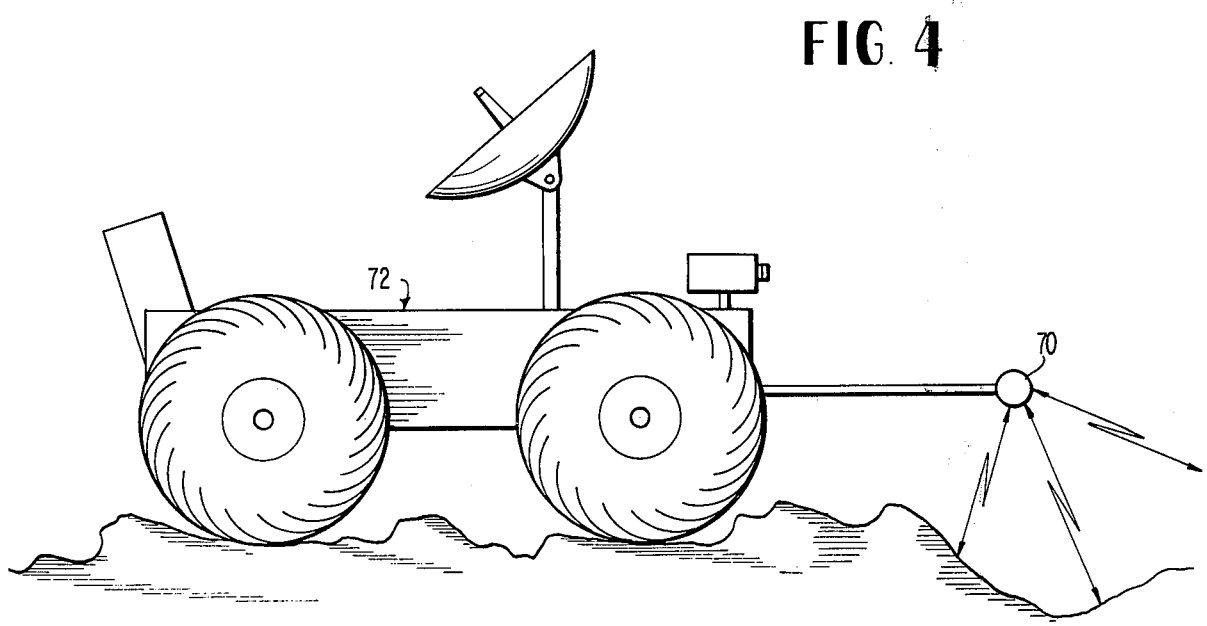
FIG. 4 illustrates a third application of the invention.

A still further application of the present invention is illustrated in FIG. 4. In FIG. 4, the invention is applied to a planetary rover. In this application the X-ray fluorescence detector 70 provides a unique combined hazard detector and surface material analyzer. As is known, certain materials fluoresce in response to X-ray excitation with predetermined fluorescence. As illustrated in FIG. 4, the detector source unit 70 may be mounted on the front of the vehicle 72. Terrain analysis may then be effectuated by determining the fluorescence and matching it to fluorescence from known materials. With the source-detector 70 mounted in front of the vehicle as shown, the sensor, or for that matter, a plurality of sensors as desired, may also map the terrain contour in front of the vehicle to permit stopping the vehicle prior to contact with excessive slopes, steep obstacles and crevices while performing a measurement of the relative abundance of elements and compounds in the surface material.

In summary, the present invention provides a significant advantage over the prior art radiation sensitive proximity sensor systems in that when used as a position or distance sensing system, it automatically discriminates between radiation from the target object as opposed to extraneous radiation. Still further, the present invention provides a significant advantage to conventional radiation responsive terrain mapping and analysis systems by recognizing that particular materials fluoresce with characteristic radiation in response to certain types of radiation excitation.

The invention has been described and illustrated with reference to a preferred embodiment thereof but it will be understood by those skilled in the art that various changes in form and detail may be made therein without departing from the spirit and scope of the invention.

What is claimed is:

1. In a terminal closure and docking alignment system for docking a monitoring vehicle with a target vehicle, radiation responsive apparatus for providing range data comrising:

a source of radiation, means for directing said radiation to said target vehicle, at least three targets arranged in a nonlinear configuration on said target vehicle, each of said targets being coated with a different fluorescent material for emitting a different characteristic fluorescence in response to said radiation, and a plurality of detectors on said monitoring vehicle equal in number to the number of said targets, each of said detectors cooperating with a single one of said targets for detecting only the characteristic fluorescence of said target.

2. The apparatus of claim 1 wherein said source of radiation is a source of nucleonic radiation.

3. The apparatus of claim 1 wherein each of said detectors comprises:

radiation filter means for passing only said characteristic fluorescence, photon detector means, responsive to the output of said filter means, for detecting said characteristic fluorescence, and counting means for producing an electrical signal indicative of the quantity of received radiation over a given time interval.

4. The apparatus of claim 3 wherein each of said detectors further includes means, responsive to said counting means, for producing an electrical signal proportional to the distance between the monitoring and target vehicles.

* * * * *